United States Patent

Meyer et al.

Patent Number: 6,156,925
Date of Patent: Dec. 5, 2000

[54] PROCESS FOR THE PREPARATION OF HALOGENATED PHENYLMALOATES

[75] Inventors: Oliver Meyer, Ingelheim; Rudi Eisenacht, Mainz, both of Germany

[73] Assignee: American Cyanamid Company, Madison, N.J.

[21] Appl. No.: 09/404,172

[22] Filed: Sep. 24, 1999

Related U.S. Application Data

[60] Provisional application No. 60/101,767, Sep. 25, 1998.

[51] Int. Cl.$^7$ .................................................. C07C 69/76
[52] U.S. Cl. ............................................................. 560/82
[58] Field of Search ................................................ 560/82

[56] References Cited

U.S. PATENT DOCUMENTS

| | | |
|---|---|---|
| 5,593,996 | 1/1997 | Pees et al. . |
| 5,612,345 | 3/1997 | Becher et al. . |
| 5,750,766 | 5/1998 | Krummel et al. . |
| 5,756,815 | 5/1998 | Knell . |
| 5,808,066 | 9/1998 | Krummel et al. . |

OTHER PUBLICATIONS

J. Setsune et al., Chemistry Letters, pp. 367–370, 1981.
R. Ugo et al., Gazetta Chimica Italiana, 122, 511–514, 1992.
G.C. Finger et al., J. Am. Chem. Soc. 73, 153–155, 1951.

*Primary Examiner*—Paul J. Killos
*Attorney, Agent, or Firm*—Charles F. Costello

[57] ABSTRACT

A process for the preparation of dialkyl phenylmalonates of formula I,

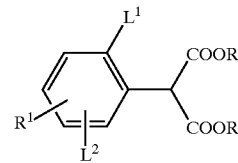

(I)

wherein R, $R^1$, $L^1$ and $L^2$ have the meaning given in the claims which comprises treating an phenylbromide of formula II

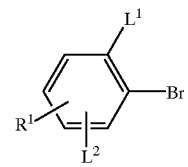

(II)

with a dialkyl malonate of formula III

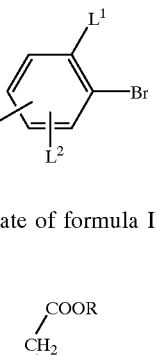

(III)

in an inert solvent in the presence of a base and a copper salt, wherein 1.0 mole of the phenylbromide of formula II is treated with the enolate obtained from 2.0 to 4.0 moles of the dialkyl malonate of formula III and 2.0 to 3.8 moles of the base.

10 Claims, No Drawings

PROCESS FOR THE PREPARATION OF HALOGENATED PHENYLMALOATES

This application claim benefit to provisional application No. 60/101,767 and filing date Sep 25, 1998.

BACKGROUND OF THE INVENTION

Halogenated phenylmalonates are useful as intermediates for the preparation of a variety of compounds which are useful as agrochemicals, pharmaceuticals or liquid crystals. In particular, they are key intermediates in the preparation of fungicidal 6-(halophenyl)-triazolopyrimidines which are described for example in EP 0 550 113 and WO 94/20501.

J. Setsune et al., Chemistry Letters, pp. 367–370, 1981 disclose a method of coupling phenylhalides with sodium diethylmalonate in the presence of copper(1) salts. However, good yields are obtainable only with phenylbromides substituted with electron withdrawing groups when 1 equivalent of phenylbromide is reacted with 1.2 equivalents of sodium diethylmalonate according to this document. Moreover, use of two equivalents of sodium diethylmalonate gave even lower yields.

The use of 5 equivalents of sodium diethylmalolanate as suggested by R. Ugo et al., Gazzefta Chimica Italiana, 122,1992, pp. 511–514, is not possible with arylbromides substituted by two or more halogen atoms, since undesired side-reactions will occur and decrease the yields.

Therefore, the methods known from the prior art are not entirely satisfactory for large scale production, since the yields of the reactions starting from halogenated phenylbromides are often low.

SUMMARY OF THE INVENTION

The present invention provides an effective and efficient process for the preparation of dialkyl phenylmalonates of formula I,

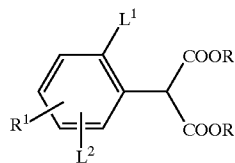
(I)

wherein
- $L^1$ and $L^2$ each independently represent a fluoro or chloro atom;
- $R^1$ represents a hydrogen or halogen atom or an alkyl or alkoxy group; and
- R represents an alkyl group, which comprises treating an phenylbromide of formula II

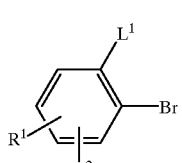
(II)

wherein $R^1$, $L^1$ and $L^2$ have the meaning given for formula II, with a dialkyl malonate of formula III

(III)

wherein R has the meaning given, in an inert solvent in the presence of a base and a copper salt, wherein 1.0 mole of the phenylbromide of formula II is treated with the enolate obtained from 2.0 to 4.0 moles of the dialkyl malonate of formula III and 2.0 to 3.8 moles of the base.

It is, therefore, an object of the present invention to provide an efficient new process for the preparation of phenylmalonates.

Other objects and advantages of the present invention will be apparent to those skilled in the art from the following description and the appended claims.

DETAILED DESCRIPTION OF THE PREFERRED EMBODIMENTS

In general terms, unless otherwise stated herein, the term alkyl as used herein with respect to a radical or moiety refer to a straight or branched chain radical or moiety. As a rule, such radicals have up to 10, in particular up to 6 carbon atoms. Suitably an alkyl moiety has from 1 to 6 carbon atoms, preferably from 1 to 3 carbon atoms. A preferred alkyl moiety is the methyl or especially the ethyl group.

Suitable bases are strong bases, preferably alkali metals, such as sodium, alkali hydrides, such as sodium or potassium hydride, alkali amides, such as sodium amide, alkali alkylamides, such as lithium diisopropylamide, alkali alkoxides such as potassium tert.-butoxide, or alkali alkanes, such as butyllithium.

Suitable copper(I) salts include copper(I) halides such as copper(I) iodide, copper(I) bromide or copper(I) chloride, copper(I)alkoxides such as copper(I) tert.-butoxide, copper (I) oxide or copper(I) tetrafluoroboate, in particular copper (I) bromide.

The term "enolate" refers to the deprotonated dialkylmalonate of formula IIIA

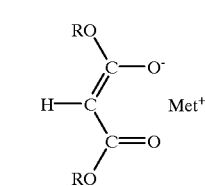
(IIIA)

wherein Met represents the metal atom of the base used or copper.

$L^2$ is preferably attached in the ortho-position with respect to the bromo atom in formula II. In a particularly preferred embodiment the reaction is carried out with 2-chloro-6-fluorobromobenzene, 2,6-difluorobromobenzene, 2,4,6-trichlorobromobenzene or 2,4,6-trifluorobromobenzene, in particular 2,4,6-trifluorobromobenzene.

Further preferred embodiments of the process according to the present invention is a process wherein:
- the base is sodium hydride;
- 1 mole of phenylbromide of formula II is treated with the enolate obtained from 2.5 to 3.5 moles of dialkyl malonate and 2.0 to 2.5 moles of the base; preferably the dialkyl malonate of formula I is used in excess with respect to the base, the molar ratio of the dialkyl malonate of formula II to the base is preferably in the range of 1:1 to 1.5 to 1, in particular in the range of 1.1:1 to 1.3:1;

a mixture consisting of the phenylbromide of formula II, the enolate obtained from the dialkyl malonate of formula III, the strong base, a copper salt, optionally a complexing agent and an inert solvent is stirred at temperatures between room temperature and 150° C.;

the inert solvent selected from the group consisting of diethylether, diisopropylether, tert-butylmethylether, 2,2-dimethoxypropane, diethoxyethane, tetrahydrofuran, tetrahydropyran and dioxane or a mixture of these solvents, in particular 1,4-dioxane;

0.05 to 1.50 mole, preferably 0.1 to 0.9 mole of the copper-(I) salt related to 1 mole of phenylbromide of formula II is used;

the copper-(I) salt is complexed by a dialkylsulphide, preferably a di-$C_{1-}$-alkylsulphide, in particular dimethylsulphide;

R represents a $C_{1-4}$ alkyl group, in particular an ethyl group;

$R^1$ is attached in the para-position with respect to the bromine atom of formula II.

The compound of formula II is preferably 2-chloro-6-fluorobromobenzene or 2,4,6-trifluorobromobenzene, which can be prepared from commercially available 1,3,5-trifluorobenzene by bromination as disclosed for example by G. C. Finger et al., J. Am. Chem. Soc. Vol 73, pp. 153–155 (1951).

As a rule the reaction between the phenylbromide and the enolate obtained from the dialkyl malonate and the strong base is carried out at elevated temperatures, preferably between 35° C. and 110° C., in particular between 50° C. and 100° C., most preferred at the reflux temperature of the reaction medium.

The reaction mixture preferably is neutralized with dilute acid, the phases are separated and the organic layer is dried and concentrated.

The crude product obtained can be purified according to standard methods for example by distillation in vacuo, chromatographic methods or crystallization.

However, the crude product obtained according to the process of this invention is pure enough to be used as intermediate without further purification.

The reaction is as a rule completed within 5 to 50 hours, in particular 10 to 25 hours.

In a particularly preferred embodiment of the process according to this invention diethyl malonate (2 to 3 moles) is added to a mixture of sodium hydride (1.5 to 2.5 moles) and 1,4-dioxane at 55 to 60° C. within 2 to 5 hours. Subsequently copper(I) bromide, optionally complexed with dimethylsulphide, (0.1 to 0.3 moles) is added. A mixture of 2,4,6-trifluorobromobenzene (1 mol) and 1,4-dioxane is added. The reaction mixture is heated to 80–120° C. for 10 to 20 hours. The reaction mixture is neutralized with a mineral acid in particular hydrochloric acid, and the organic phase is separated off and the aqueous phase is extracted. The combined organic phases are concentrated in vacuo. The residue is filtered, washed with an organic solvent and the solvent is distilled off. The residue is distilled in vacuo.

In order to facilitate a further understanding of the invention, the following illustrative examples are presented. The invention is not limited to the specific embodiments described or illustrated, but encompasses the full scope of the appended claims.

EXAMPLE 1

Preparation of diethyl 2,4,6-trifluorophenylmalonate

Diethyl malonate (6.21 mol) is added to a mixture of sodium hydride (5.13 mol) and 1,4-dioxane (1400 ml) at 55 to 60° C. within 3 hours. The mixture is stirred for 10 minutes at 55° C. and copper(l) bromide (0.5 mol) is added. A mixture of 2,4,6-trifluorobromobenzene (2.50 mol) and 1,4-dioxane (600 ml) is added. The reaction mixture is heated at 100° C. for 14 hours and cooled to 15° C. Hydrochloric acid (12N, 350 ml) is added slowly at 15 to 20° C. The organic phase is separated off and the aqueous phase is extracted with ethyl acetate (250 ml) and toluene (200 ml). The combined organic phases are concentrated in vacuo. The residue is filtered over silica gel, washed with petroleum ether/ethyl acetate (15:1) and the solvent is distilled off. The residue is distilled in vacuo to yield 540 g of the product as a white solid. Bp.: 88–105° C. at 0.1 mbar; mp.: 50° C. Analogously are prepared dimethyl 2,4,6-trifluorophenylmalonate, diethyl 2,6-difluorophenylmalonate, diethyl 2-chloro-6-fluorophenylmalonate, diethyl 2,4,5-trifluorophenylmalonate, bp.: 100° C. at 0.006 mbar; diethyl 2,4,6-trichlorophenylmalonate, bp.: 144–150° C. at 0.4 mbar; diethyl 2,3,4-trifluorophenylmalonate, bp.: 94° C. at 0.003 mbar;

EXAMPLES 2 AND 3

Preparation of diethyl 2,4,6-trifluorophenylmalonate

Analogously to example 1 2,4,6-trifluorobromobenzene is treated with sodium diethylmalonate in different amounts.

The relative amounts of the reactants and solvents, the reaction temperature and yields are shown in table I in which the following abbreviations have been used:

| TFBB | 2,4,6-trifluorobromobenzene |
| DMS | dimethylsulphide |
| cat. | catalyst |
| am_cat | amount of catalyst |
| time | reaction time |
| DEM | diethyl malonate |

TABLE I

| | | Examples 2 and 3 | | | | | |
| Example | cat | TFBB (mmol) | am_cat (mmol) | NaH (mmol) | DEM (mmol) | Time (hrs) | Yield (%) |
| --- | --- | --- | --- | --- | --- | --- | --- |
| 2 | CuBr/DMS | 23.7 | 28.9 | 57.8 | 57.8 | 14 | 68 |
| 3 | CuBr/DMS | 23.7 | 28.4 | 56.9 | 69.4 | 14 | 77 |

COMPARISON EXAMPLES A TO D

Preparation of diethyl 2,4,6-trifluorophenylmalonate

Analogously to example 1,2,4,6-trifluorobromobenzene is treated with 1.22 equivalents of sodium diethylmalonate under different conditions.

The relative amounts of the reactants and solvents, the reaction temperature and yields are shown in table II.

TABLE II

Comparison Examples A to D

| Example | cat | TFBB (mmol) | am_cat (mmol) | NaH (mol) | DEM (mol) | Time (hrs) | Yield (%) |
|---|---|---|---|---|---|---|---|
| A | CuBr/DMS | 23.7 | 28.9 | 28.9 | 28.9 | 6 | 35 |
| B | CuBr/DMS | 23.7 | 28.9 | 28.9 | 28.9 | 14 | 45 |
| C | CuBr | 23.7 | 28.9 | 28.9 | 28.9 | 14 | 41 |
| D | CuBr/DMS | 23.7 | 28.9 | 57.8 | 28.9 | 14 | traces |

What is claimed is:

1. A process for the preparation of dialkyl phenylmalonates of formula I,

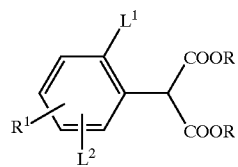

(I)

wherein $L^1$ and $L^2$ each independently represent a fluoro or chloro atom;

$R^1$ represents a hydrogen or halogen atom or an alkyl or alkoxy group; and

R represents an alkyl group, which comprises treating an phenylbromide of formula II

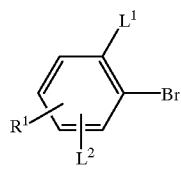

(II)

wherein $R^1$, $L^1$ and $L^2$ have the meaning given for formula I, with a dialkyl malonate of formula III

(III)

wherein R has the meaning given, in an inert solvent in the presence of a base and a copper salt, wherein 1.0 mole of the phenylbromide of formula II is treated with the enolate obtained from 2.0 to 4.0 moles of the dialkyl malonate of formula III and 2.0 to 3.8 moles of the base.

2. A process according to claim 1, wherein the base is sodium hydride.

3. A process according to claim 1, wherein 1 mole of phenylbromide of formula II is treated with thnolate obtained from 2.5 to 3.5 moles of dialkyl malonate and 2.0 to 2.5 moles of the base.

4. A process according to claim 1, wherein a mixture consisting of the phenylbromide of formula II, the enolate obtained from the dialkyl malonate of formula III, the strong base, a copper salt, optionally a complexing agent and an inert solvent is stirred at temperatures between 30° C. and 150° C.

5. A process according to claim 4, wherein the inert solvent selected from the group consisting of diethylether, diisopropylether, tert-butylmethylether, 2,2-dimethoxypropane, diethoxyethane, tetrahydrofuran, tetrahydropyran and dioxane or a mixture of these solvents.

6. A process according to claim 1, wherein 0.05 to 1.50 mole of the copper-(I) salt related to 1 mole of phenylbromide of formula II is used.

7. A process according to claim 1, wherein the copper-(I) salt is complexed by a dialkylsulphide.

8. A process according to claim 1, wherein R represents a $C_{1-4}$ alkyl group.

9. A process according to claim 1, wherein $R^1$ is attached in the para-position with respect to the bromine atom of formula II.

10. A process according to claim 9, wherein the compound of formula II is 2,4,6-trifluorobromobenzene or 2-chloro-6-fluorobromobenzene.

* * * * *